US012090317B2

(12) United States Patent
Rickert et al.

(10) Patent No.: US 12,090,317 B2
(45) Date of Patent: Sep. 17, 2024

(54) ADAPTIVE DEEP BRAIN STIMULATION OF THE SUPEROLATERAL MEDIAL FOREBRAIN BUNDLE

(71) Applicant: CorTec GmbH, Freiburg (DE)

(72) Inventors: Joern Rickert, Freiburg (DE); Martin Schuettler, Emmendingen (DE); Volker A. Coenen, Bollschweil (DE); Thomas Schlaepfer, Freiburg (DE); Michael Tangermann, Waldkirch (DE)

(73) Assignee: CorTec GmbH, Freiburg (DE)

( * ) Notice: Subject to any disclaimer, the term of this patent is extended or adjusted under 35 U.S.C. 154(b) by 133 days.

(21) Appl. No.: 17/520,092

(22) Filed: Nov. 5, 2021

(65) Prior Publication Data
US 2022/0054822 A1    Feb. 24, 2022

Related U.S. Application Data

(63) Continuation of application No. PCT/EP2020/062924, filed on May 8, 2020.

(30) Foreign Application Priority Data

May 8, 2019  (DE) .................... 20 2019 102 592.1

(51) Int. Cl.
*A61N 1/05* (2006.01)
*A61N 1/36* (2006.01)
(Continued)

(52) U.S. Cl.
CPC ....... *A61N 1/0534* (2013.01); *A61N 1/36139* (2013.01); *A61N 1/36167* (2013.01);
(Continued)

(58) Field of Classification Search
CPC .............. A61N 1/0534; A61N 1/37514; A61N 1/36096; A61B 5/165; A61B 5/6868
See application file for complete search history.

(56) References Cited

U.S. PATENT DOCUMENTS

| | | | |
|---|---|---|---|
| 2005/0049651 | A1 | 3/2005 | Whitehurst et al. |
| 2007/0027500 | A1 | 2/2007 | Maschino et al. |
| 2012/0016435 | A1* | 1/2012 | Rom .................. A61N 1/36082 607/45 |

FOREIGN PATENT DOCUMENTS

WO    2010/109448 A1    9/2010

OTHER PUBLICATIONS

International Search Report issued for corresponding International Application No. PCT/EP2020/062924 mailed on Aug. 11, 2020.
(Continued)

*Primary Examiner* — Tammie K Marlen
(74) *Attorney, Agent, or Firm* — Myers Wolin, LLC

(57) ABSTRACT

A system for brain stimulation of a patient is provided, the system having an implantable stimulator, at least one sensor component for acquiring at least one measure indicative of patient's mood, and at least one implantable stimulation electrode, designed for providing electrical pulses stimulating inside the patient's brain. The at least one stimulation electrode is connectable, through an implantable connector, to the implantable stimulator, the implantable stimulator having at least one programmable channel for conducting the electrical stimulation pulses to the at least one stimulation electrode, and being adapted for receiving continuous input signals from the at the least one sensor component. The system also has a computational unit for processing the at least one measure, and a patient's body external control interface (5) for patient and/or physician interactions.

11 Claims, 3 Drawing Sheets

(51) Int. Cl.
*A61N 1/375* (2006.01)
*A61N 1/378* (2006.01)
(52) U.S. Cl.
CPC ....... *A61N 1/37514* (2017.08); *A61N 1/3752* (2013.01); *A61N 1/3787* (2013.01)

(56) References Cited

OTHER PUBLICATIONS

Notice of the First Office Action issued by the Chinese Intellectual Property Office for CN Patent Application No. 202080034286.9, dated Nov. 9, 2023, with machine-generated English translation attached.

\* cited by examiner

ADAPTIVE DEEP BRAIN STIMULATION OF THE SUPEROLATERAL MEDIAL FOREBRAIN BUNDLE

CROSS REFERENCE TO RELATED APPLICATIONS

This application is a continuation of International Application No. PCT/EP2020/062924, filed on May 8, 2020, which takes priority from German Patent Application No. 20 2019 102 592.1, the contents of each of which are incorporated by reference herein.

TECHNICAL FIELD

The present invention relates to a system for closed-loop brain stimulation, in particular for changing the mood of a patient.

BACKGROUND

State of the Art

Deep brain stimulation has become a standard treatment for advanced stages of Parkinson's disease, and other movement disorders like tremor of various origin and dystonia. Recent research has demonstrated the feasibility of a treatment of severe mood disorders, like major depression and obsessive compulsive disorder (OCD) by brain stimulation. All studies that were conducted hitherto utilized a continuous open-loop stimulation (on or off) with standard deep brain stimulation (DBS)-electrodes. Open-loop stimulation means that the stimulation is applied to the patient using predefined stimulation patterns and according to a predefined time schedule, independent of the actual emotional state of the patient at a given time, independent of the effect of the stimulation, and independent of other reactions of the patient. In other words, there is no feed-back from the patient to the stimulation system.

Problems

Although continuous stimulation in a deep-seated brain region like the superolateral medial forebrain bundle (slMFB) with projections to the frontal lobes has proven its effectiveness in several case series of severely depressed patients, there theoretically could be to a stimulation-related lack of emotional flexibility in these patients because of the continuous neuromodulation of the reward system. This means that patients might react lesser or to a lesser extent to emotional external and internal (positive and negative) stimuli, see FIG. 3. A continuous stimulation furthermore does not consider the occurring changes in mood and does not allow the patient to adequately undulate with his emotional perception. This might result in inadvertent over- or under-stimulation depending on the patient's current emotional state. Also, a continuous stimulation could potentially lead to adaptation of the brain to the stimulation.

Another problem in particular with patients suffering from a mood disorder, which may suddenly appear, is to derive this disorder from patient's brain signals or activity. This, because the brain signals representing a "normal", non-pathologic state of a particular patient may vary over time. That is, signals representing the normal state art one specific time may not represent the normal state at another, later time anymore, the signals are said to be "floating".

On the other hand, it may be difficult to differentiate between a neural activity representing a normal change in mood caused e.g., by the patient experiencing a sudden dramatic event or just a sadness which may disappear within a certain time without being treated, and a pathologic change in mood indicating the begin of a serious depression which requires to be treated. Both cases may show the same activity.

Hereby it is to be noted that certain variations in mood should be considered to be normal, at least if they are triggered by some kind of "external" event and disappear within a given time period. Such variations in mood should not be suppressed.

Yet a further difficulty is to find out for a patient seeking the for the first time for a neural stimulation therapy, how the signals representing a normal state should look like, since the neural signals of the very same patient have never been recorded before.

It is then particularly difficult to decide when the stimulation should be terminated.

SUMMARY

The problem may be addressed by a system according to the claims.

Thus, this disclosure proposes a system and method for detecting the mood of a patient, and a comprehensive multicomponent system affording an adaptive brain stimulation where the stimulation is varied dependent on certain measures indicative of the current capacity of the patient's system in the brain that reacts to changing emotional stimuli.

This multicomponent system offers the technical possibility to acquire different physiologic and physical entities (measures) which in combination may be representative of the mental state of the patient.

BRIEF DESCRIPTION OF THE DRAWINGS

The invention will be described in more detail in connection with the Figures, wherein.

DETAILED DESCRIPTION

Figure 1:
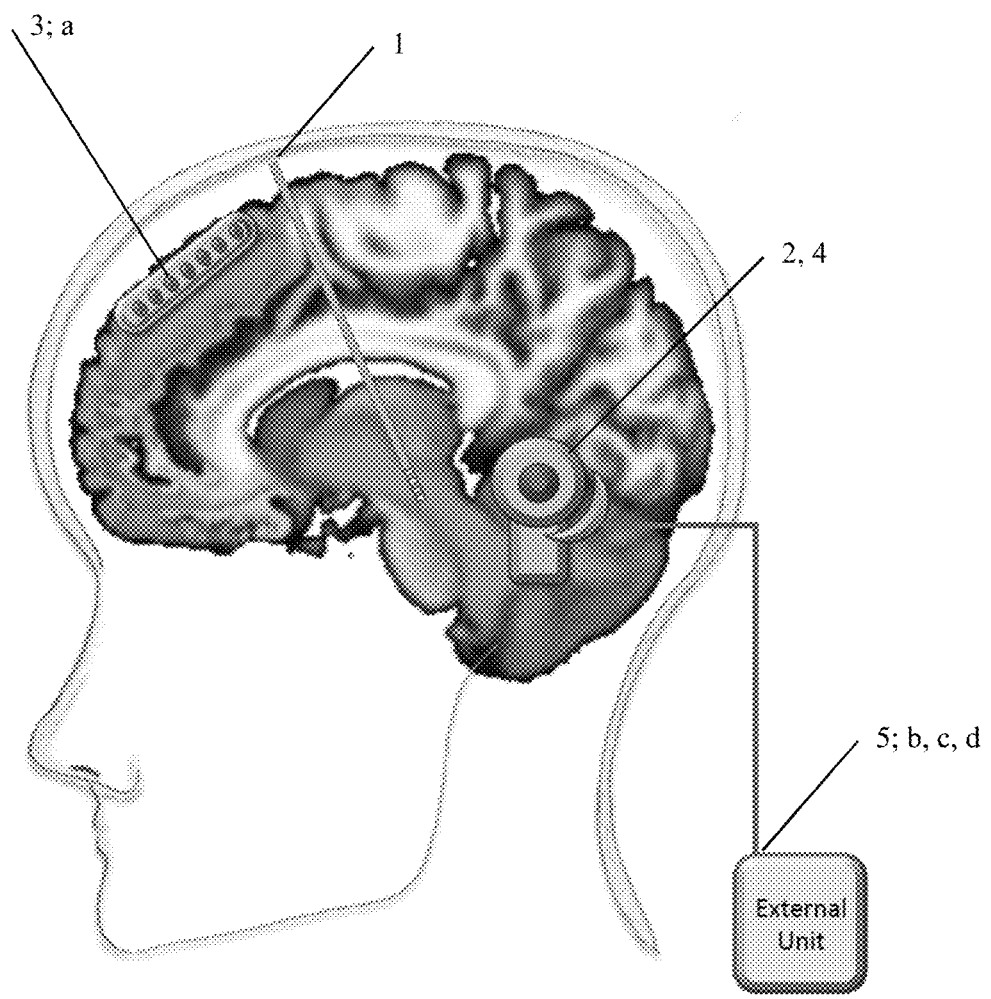
FIG. 1 illustrates principal elements of the invention of the system according to the invention.

In FIG. 1, principal elements of the invention are illustrated. That is, the system for brain stimulation of a patient comprises:

- a stimulator 2 which is implantable into the patient's body,
- at least one sensor component 3 for acquiring at least one measure a, b, c, d indicative of patient's mood,
- at least one implantable stimulation electrode 1, designed for providing electrical pulses stimulating inside the patient's brain. The at least one stimulation electrode 1 is connectable, through an implantable connector, to the implantable stimulator 2. The implantable stimulator 2 has at least one programmable channel for conducting the electrical stimulation pulses to the at least one stimulation electrode 1, and is adapted for receiving continuous input signals from the at the least one sensor component 3, and
- a computational unit 4 for processing the at least one measure a, b, c, d, and a patient's body external control interface 5 for patient and/or physician interactions.

The inventive system can be configured for adaptive sIMFB DBS for therapy of major depression.

Preferably, all measures a, b, c, d are acquired and processed.

Figure 2:
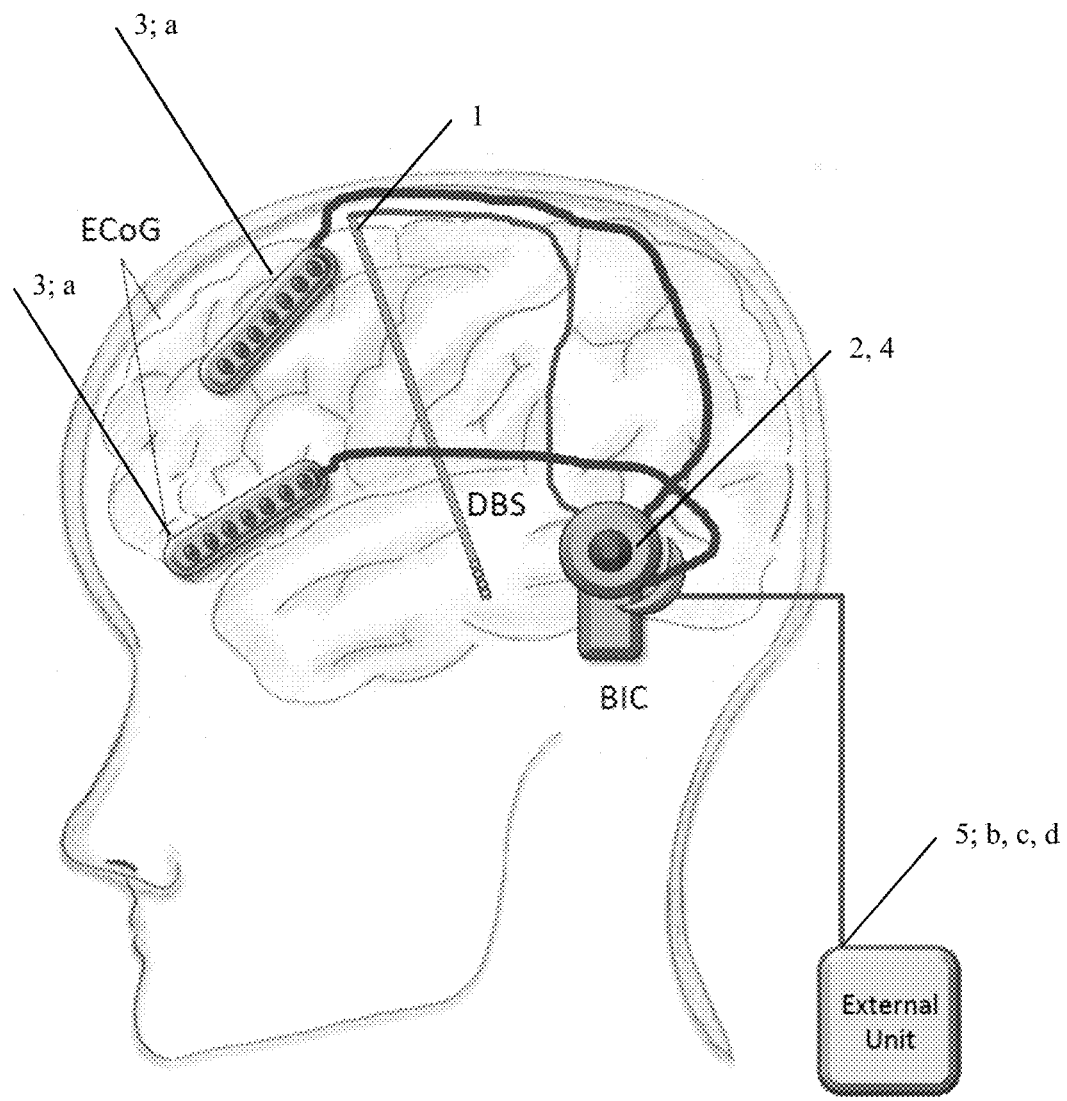
FIG. 2 illustrates a second exemplary configuration of an adaptive slMFB DBS for therapy of major depression.
Figure 3:
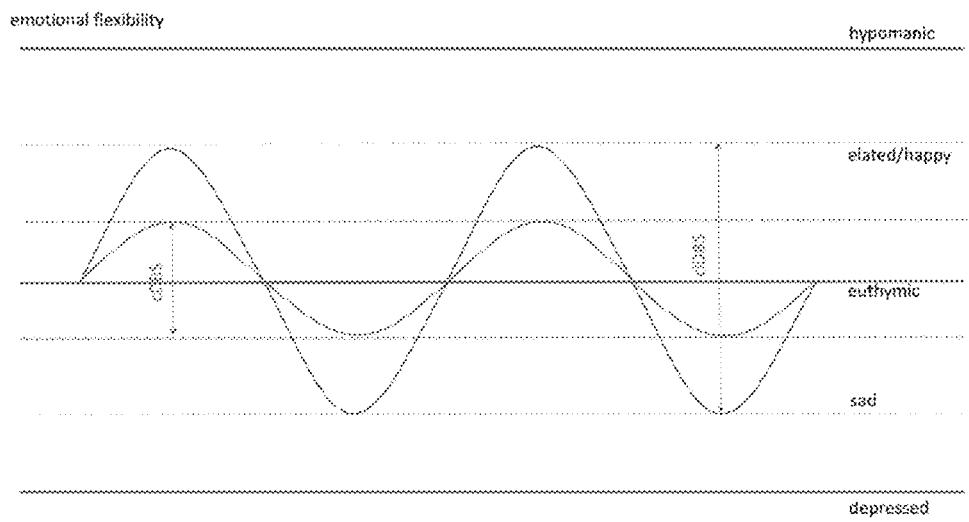
FIG. 3 illustrates patient's reaction to emotional stimuli.

FIG. 2 illustrates an exemplary configuration for such an adaptive sIMFB DBS. Hereby, FIG. 2 illustrates the interconnections between the components of the system.

The measures a, b, c, d indicative of the current capacity of the patient's system in the brain can be related to one or more of the following physiologic and physical entities:

a. Electrical activity of the brain, in particular:
  1) . . . measured by Electrocorticography on the surface of the cortex,
  2) . . . located in the prefrontal cortex contralateral to the dominant hand,
  3) . . . power of oscillations in the β and γ or other frequency ranges
  4) . . . relative to the subject's average motor activity level.
b. Level of motor activity, in particular:
  1) . . . measured by accelerometers
  2) . . . relative to the subject's average motor activity level (i.e. the subject is walking faster or slower than normal)
c. Melody of the patient's speech (expression of emotion through affective prosody, non-linguistic properties of speech), in particular:
  1) . . . measured by one or more microphones,
  2) . . . measured by one or more implanted microphones,
  3) . . . relative to the subject's average speech melody,
  4) . . . calculated from the speech speed or level of monotony (in depression for example, depressive phases are accompanied by slower and more monotonous speech melody).
d. Information from the current environment of the patient, in particular:
  1) . . . light conditions
  2) . . . social activity
  3) . . . body posture.

For measures a4, b2 and c3 the system is calibrated before treatment start in order to determine the relevant average activity levels. That is, the calibration should be started with a patient being in a normal, non-pathologic state.

Hereby, it is advantageous to understand first which of the parameters is most reflecting the patient's degree of depression (or predicts changes in affective state best). This calibration can be done together with a physician or by the patient alone after instruction. For example, in major depression disease severities can be classified according to the Montgomery-Asberg-Depression-Rating-Scale (MADRS) which can then be correlated with each measure of the system.

If the system comprises more than one measure a, b, c, d indicative for the patient's emotional state in the calibration phase, every measure is correlated with the mood of the patient measured at different times and at different states of mood. The better a measure either predicts (ideally, see below) or correlates in time with the different states of mood, the stronger its effect on the resulting stimulation will be. After initial calibration, such a calibration phase will either be repeated from time to time in order to verify and possibly adapt each measure's effect on the stimulation, or will be conducted continuously and automated by regular input to the system: this input can be provided by clinicians during regular visits of the patient, the patient itself or other persons regularly interacting with the patient.

One advantage of the continuous measurement of the patient's mood by these measures is that clinically significant changes in mood can be detected as early as possible in order to be able to deliver the therapeutic stimulation as early as possible, i.e. before a pathologic state of mood is reached, and with as little electrical stimulation as possible.

The result of the initial calibration of the system is that one or more indicators (markers) are found which are representative of the mood of the individual patient. The indicators (markers) define the state of the patient. By correlating these indicators with the mood of the patient, a baseline of the electrical activity, representing a normal, non-pathological state can be derived.

This baseline of activity will be the target mental activity to be achieved by stimulation. That is, the system is adapted for delivering stimulation to the patient until the mental activity reaches the baseline.

Next, the stimulation part of the system will be described.

According to the one general aspect of the invention, the system comprises:

(1) One or more stimulation electrodes, preferably designed for stimulating inside the brain (DBS), connected, preferably through an implantable connector, to
(2) an implantable stimulator,
  a. having one but preferably at least two independently programmable channels for conducting electrical stimulation to the one or more stimulation electrodes 1, typically in the form of charge balanced pulses delivered at frequencies between 30 and 180 Hz, preferably at 130 Hz,
  b. receiving continuous input signals from at least one other component containing one or more of the measures mentioned above under items a-d;
(3) One or more sensors for recording one or more of the measures mentioned above under items a-d;
(4) A computational unit for processing the measures mentioned above under items a-d;
(5) A body external control interface for patient and physician interactions.

According to particularly advantageous embodiments of the invention, the system can have different variants:

The stimulator 2 comprises either a battery for power supply or a coil for receiving power by induction from another coil on the outside of the skin above it.

The sensor for recording measure a (brain activity), if present, is directly connected to the stimulator 2. In this case the stimulator 2 contains a built-in amplifier and AD-converter for the recorded signal.

The sensors for recording the measures b-c are also directly connected to the stimulator 2 if the sensors are implanted in the body. The stimulator 2 then comprises built-in amplifier and an AD-converter for these signals. If these sensors are not implanted sensors, they are connected to the body external control interface 5.

A sensor for recording the measure d (environment) is connected to the body external control interface 5.

The computational unit 4 can be on the implantable stimulator 2 or on the body external control interface.

The computational unit 4 can be a static algorithm that only changes through calibration, or it can be an autonomously adapting algorithm.

The measures as mentioned above correlate with the mental state of the patient. Changes in mental state may be reflected in changes of some or all of these measures. Hereby, some of the measures may change faster or earlier than other measures dependent on the mood of the patient. In particular, the mental activity changes faster than e.g., voice or movement of the person. By detection of such changes, an upcoming depression can be achieved.

The system may be configured to work as follows. First, the system performs a calibration phase where, for a patient in normal, non-pathologic (i.e., non-depressive) state, the reference measures a4, b2 and c3 as described above are taken. Reference activity levels are determined.

Once the system is calibrated for a patient, the system is ready for being used in treating depression. The system continuously collects via its sensors measures from the patient. As long as the measures are within predetermined tolerance ranges around the average levels determined during calibration, no stimulation intervention is started. The patient is allowed to have different states of mood, as long as the patient comes down to a normal state within a predefined time.

The system is configured to start stimulation as soon as the measures deviate by more than the tolerance ranges define. The system is configured to select amplitude and frequency of the stimulation depending on the deviation of the measures from the average level. E.g., the more the measures deviate, the larger the amplitude of the stimulation pulses is set.

The system is configured to measure the mental activity continuously during the stimulation therapy. The more the mental activity and other measures approach to the respective average level, the more the stimulation amplitudes are lowered.

Furthermore disclosed is a method for brain stimulation of a patient, comprising:
  acquiring, by at least one sensor component 3, at least one measure a, b, c, d indicative of patient's mood,
  stimulating the patient's brain, by at least one stimulation electrode 1, preferably designed for being placed inside the patient's brain,
  the at least one stimulation electrode 1 being connectable, preferably through an implantable connector, to an implantable stimulator 2,
  conducting, by the stimulator 2, electrical stimulation to the at least one stimulation electrode 1, the stimulator having at least one programmable channel for, and
  receiving, by the stimulator 2, continuous input signals from the at the least one sensor component 3,
  processing, by a computational unit 4, the at least one measure a, b, c, d.
  interacting, via a patient's body external control interface 5, with the stimulator.

The at least one measure a, b, c, d may relate to at least one, preferably to all, of
  patient's brain electrical activity a,
  level of patient's motor activity b,
  melody of patient's speech c,
  patient's environment d.

The method may further comprise supplying power to the stimulator 2 via a battery or a coil for receiving power by induction from another coil on the outside of the skin.

The measures relating to the level b and/or the melody c may be acquired by a sensor component 3 implanted in patient's body and connected able to the stimulator 2.

The measures relating to the level b and/or the melody c may be acquired by a sensor component 3 which is adapted to be body-external, and is connected to the body external control interface 5.

Acquiring the measures relating to environment d may performed by a sensor component 3 which is connected to the body external control interface 5.

In the method, the computational unit 4 may apply one of
  a static algorithm that is adaptable through calibration, and
  an autonomously adapting algorithm for providing the stimulation pulses.

In the method, pulses may be provided, the stimulator 2, in the form of charge balanced pulses at frequencies between 30 and 180 Hz, preferably at 130 Hz.

What is claimed is:

1. A system for brain stimulation of a patient, comprising:
  an implantable stimulator,
  at least one sensor component configured for acquiring a measure indicative of a mood of the patient, the at least one sensor component comprising one or more microphone configured to acquire the patient's melody of speech,
  a computational unit configured for processing the acquired measure,
    wherein the computational unit is configured to apply a static algorithm that is adaptable to an individual patient through calibration,
    wherein the calibration comprises a process of deriving, for the patient in a normal mental condition and without conducting stimulation pulses, for the measure, a corresponding average level, and of storing the corresponding average level in correlation with a normal state of the patient, and
    wherein the computational unit is further configured to generate stimulation pulses if the acquired measure deviates by at least a predetermined amount from the stored corresponding average level, and to stop generating stimulation pulses if the acquired measure does not deviate by the predetermined amount from the stored corresponding average level,
  at least one implantable stimulation electrode, designed for providing electrical pulses stimulating inside the patient's brain, the at least one stimulation electrode being connectable, through an implantable connector, to the implantable stimulator,
  the implantable stimulator having at least one programmable channel configured for conducting the generated electrical stimulation pulses to the at least one stimulation electrode, and
    being adapted for receiving continuous input signals from the at the least one sensor component,
  and
  a patient's body external control interface for patient and/or physician interactions.

2. The system of claim 1, wherein the at least one sensor component is further adapted for acquiring a measure indicative of least one of
  brain electrical activity of the patient,
  level of motor activity of the patient, and
  environment of the patient.

3. The system of claim 2, wherein
  the sensor component is further adapted for recording the measure indicative of brain activity of the patient and is connectable to the implantable stimulator.

4. The system of claim 3, wherein
the implantable stimulator contains a built-in amplifier and AD-converter for the recorded measure.

5. The system of claim 1, wherein
the implantable stimulator comprises a battery for power supply or a coil for receiving power by induction from another coil arranged outside of skin of the patient.

6. The system of claim 1, wherein the sensor component is further adapted for acquiring a measure indicative of a level of motor activity of the patient, and is implantable in the body of the patient and is connectable to the implantable stimulator and to the body external control interface.

7. The system of claim 1, wherein the computational unit is located on the implantable stimulator or on the body external control interface.

8. The system of claim 1, wherein the computational unit is configured to apply an autonomously adapting algorithm for providing stimulation pulses.

9. The system of claim 8, further adapted to select amplitude and/or frequency of the pulses depending on a deviation of the measure from a stored corresponding average level.

10. The system of claim 1, wherein the implantable stimulator is adapted to provide pulses in the form of charge balanced pulses at frequencies between 30 and 180 Hz.

11. The system of claim 1, further configured to acquire perform the measure continuously during brain stimulation.

* * * * *